United States Patent
Palla-Venkata et al.

(10) Patent No.: US 8,648,024 B2
(45) Date of Patent: Feb. 11, 2014

(54) HYDROPHOBIC SILICAS AS SQUEAKINESS ENHANCERS IN CLEANSING COMPOSITIONS

(75) Inventors: Chandra Sehkar Palla-Venkata, Trumbull, CT (US); Surajit Mukherjee, Trumbull, CT (US); Wei Dong Tian, West Roxbury, MA (US); Martin Swanson Vethamuthu, Southbury, CT (US); Rajendra Mohanlal Dave, Trumbull, CT (US); Junqi Ding, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 68 days.

(21) Appl. No.: 13/370,707

(22) Filed: Feb. 10, 2012

(65) Prior Publication Data
US 2013/0210694 A1    Aug. 15, 2013

(51) Int. Cl.
*C11D 1/90* (2006.01)
*C11D 3/04* (2006.01)
*C11D 3/08* (2006.01)

(52) U.S. Cl.
USPC ........... 510/123; 510/130; 510/135; 510/136; 510/137; 510/138; 510/141; 510/158; 510/159; 510/501; 510/511; 424/70.12; 424/70.122; 424/70.21

(58) Field of Classification Search
USPC ......... 510/123, 130, 135, 136, 137, 138, 141, 510/158, 159, 501, 511; 424/70.12, 70.122, 424/70.21
See application file for complete search history.

(56) References Cited

U.S. PATENT DOCUMENTS

| | | | |
|---|---|---|---|
| 3,538,230 A | 11/1970 | Pader et al. | |
| 4,485,089 A | 11/1984 | Leipold | |
| 4,719,030 A | 1/1988 | Williams et al. | |
| 5,653,970 A * | 8/1997 | Vermeer | 424/70.24 |
| 5,658,577 A * | 8/1997 | Fowler et al. | 424/401 |
| 8,053,400 B2 * | 11/2011 | Dong et al. | 510/125 |
| 2002/0039976 A1 | 4/2002 | Sebillotte-Arnaud et al. | |
| 2003/0134761 A1 | 7/2003 | Sebillotte-Arnaud et al. | |
| 2003/0236179 A1 | 12/2003 | Bodet et al. | |
| 2004/0186030 A1 | 9/2004 | Hofrichter et al. | |
| 2005/0192190 A1 | 9/2005 | Hasenzahl et al. | |
| 2006/0030501 A1 | 2/2006 | Niebauer | |
| 2006/0246027 A1 | 11/2006 | Tanner | |
| 2006/0280706 A1 | 12/2006 | Sebillotte-Arnaud | |
| 2007/0036736 A1 | 2/2007 | Kalla et al. | |
| 2008/0008672 A1 | 1/2008 | Tobita | |
| 2009/0252691 A1 | 10/2009 | Gartstein et al. | |
| 2009/0325837 A1 | 12/2009 | Mundschau et al. | |
| 2010/0111887 A1 | 5/2010 | Senee et al. | |

OTHER PUBLICATIONS

Co-pending U.S. Appl. No. 13/370,733, filed Feb. 10, 2012; titled "Calcium and Magnesium Salts as Squeakiness Enhancers in Cleansing Compositions".

* cited by examiner

*Primary Examiner* — Gregory Delcotto
(74) *Attorney, Agent, or Firm* — Karen E. Klumas

(57) ABSTRACT

A cleanser composition is provided which includes:
(i) from 0.01 to 5% by weight of a hydrophobic or cationic silica having a number average particle size ranging from 1 to 30,000 nm;
(ii) from 0.1 to 30% by weight of a non-soap synthetic surfactant; and
wherein the composition exhibits a UMT Test number of rubs to stick-slip from 1 to 12 under a 20 g load, and a foam volume ranging from 200 to 800 ml using a SITA Foam Tester.

9 Claims, No Drawings

//HYDROPHOBIC SILICAS AS SQUEAKINESS ENHANCERS IN CLEANSING COMPOSITIONS

BACKGROUND OF THE INVENTION

1. Field of the Invention

The present invention relates to skin and hair cleansing compositions in toilet bar, body wash, liquid hand cleanser, shampoo and related products.

2. The Related Art

Soap has been a mainstay active for cleansers. It is cheap and efficient. But it can be harsh on the skin. Synthetic surfactants have been introduced as replacements for soap. Some of these generate lather equivalent to that of soap and have the further benefit of being milder.

Often the skinfeel properties of a synthetic surfactant are quite different than that of soap. Indeed, generally as mildness increases, the deposition of the synthetic surfactant and other moisturizers increases. This forms a protective barrier to the stripping of natural oils and fats from the epidermis.

A majority of consumers in Japan, and many in other countries, find the feel of synthetic detergents to be lacking. They consider moisturizing deposits as a sign of cleaning inefficiency. They need to be reassured of cleanliness by the traditional squeaky non-lubricated feel of soap.

SUMMARY OF THE INVENTION

A cleanser composition is provided which includes:
(i) from 0.01 to 5% by weight of a hydrophobic or a cationic silica having a number average particle size ranging from 1 to 30,000 nm;
(ii) from 0.1 to 30% by weight of a non-soap synthetic surfactant; and
wherein the composition exhibits a UMT Test number of rubs to stick-slip ranging from 1 to 12 under a 20 g load, and a foam volume ranging from 200 to 800 ml using a STA Foam Tester.

DETAILED DESCRIPTION OF THE INVENTION

Now it has been found that small amounts of hydrophobic or cationic silicas can add squeakiness to the feel of non-soap synthetic surfactant containing cleansing systems while not detracting from mildness. Squeakiness has been correlated by us to the output from a Tribometer UMT friction/stick-slip tester. This instrument measures the change in number of rubs to onset of stick-slip between a base formula and a sample composition. Squeakiness is evidenced relative to the base formula by number of rubs to stick-slip ranging from 1 to 12, preferably from 3 to 10, optimally from 4 to 8, under a 20 g load.

By the term "hydrophobic silica" is meant a silica which has been coated with a hydrophobic material such as a silicone oil, a fatty acid ester, a wax or a hydrocarbon. Particularly desirable are silicas which have been silylated with a reactive silicone gas or liquid such as trimethyl silyl chloride. A representative example of hydrophobic silica is Aerogel VM-2270® sold by the Dow Corning Corporation. This material has an average particle size ranging from 5,000 to 15,000 nm and a bulk density ranging from 40 to 100. Another useful hydrophobic silica is Aerosil R 972® available from Evonik Corporation, and having an average particle size of 16 nm.

By the term "cationic silica" a silica having a zeta potential (surface charge) of at least +10 mV, particularly a zeta potential ranging from +10 to +200, more preferably from +15 to +100, and optimally from +15 to +50 mV, as measured in a DT-1200 test, CVI-method, at pH 3.0. A representative example of a cationic silica is Aerodisp WK341, a trade mark of Degussa.

Amounts of the hydrophobic or cationic silica in the cleanser compositions may range from 0.01 to 5%, preferably from 0.5 to 3%, and optimally from 0.8 to 3% by weight.

Another component of compositions disclosed herein are non-soap synthetic foaming surfactants. These may be selected from anionic, cationic, amphoteric and combination surfactants thereof. Amounts may range from 0.1 to 30%, preferably from 1 to 20%, and optimally from 3 to 15% by weight of the composition.

Suitable amphoteric surfactants for use herein include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative amphoterics are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, cocoamphoacetates, and mixtures thereof. The sulfobetaines may include stearyl dimethyl sulfopropyl betaine, lauryl dimethyl sulfoethyl betaine, lauryl bis-(2-hydroxyethyl) sulfopropyl betaine and mixtures thereof. Most preferred is cocoamidopropyl betaine.

The anionic surfactant may be, but is not limited to, $C_8$-$C_{22}$ alkane sulfates, ether sulfates and sulfonates. Among the suitable sulfonates are primary $C_8$-$C_{22}$ alkane sulfonate, primary $C_8$-$C_{22}$ alkane disulfonate, $C_8$-$C_{22}$ alkene sulfonate, $C_8$-$C_{22}$ hydroxyalkane sulfonate or alkyl glyceryl ether sulfonate.

Specific examples of anionic surfactants suitable for use herein include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof.

Of particular advantage as a synthetic anionic surfactant are the $C_8$-$C_{22}$ acyl glycinate salts. Suitable glycinate salts include sodium cocoylglycinate, potassium cocoylglycinate, sodium lauroylglycinate, potassium lauroylglycinate, sodium myristoylglycinate, potassium myristoylglycinate, sodium palmitoylglycinate, potassium palmitoylglycinate, sodium stearoylglycinate, potassium stearoylglycinate, ammonium cocoylglycinate and mixtures thereof. Cationic counterions to form the salt of the glycinate may be selected from sodium, potassium, ammonium, alkanolammonium and mixtures of these cations.

Nonionic surfactants which may be used include the reaction products of compounds having a hydrophobic group and a reactive hydrogen atom. Exemplative are alcohols, acids, amides or alkyl phenols reacted with alkylene oxides, especially ethylene oxide either alone or with propylene oxide. Specific nonionics are $C_6$-$C_{22}$ alkyl phenols-ethylene oxide condensates, the condensation products of $C_8$-$C_{18}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides. Also useful are the alkyl polysaccharides.

Surfactants should be chosen which will allow the compositions to have a SITA Foam Test Value ranging from 200 to 800, preferably from 300 to 700, and optimally between 400 and 600 ml. SITA Foam Tester R-2000 Model from the Future Digital Scientific Corp. is normally utilized for this evaluation. The experiment protocol includes loading 10 g of product (no pre-dilution) into a measuring cylinder. Thereinto is added 250 ml water at 40-45° C. The foam volume is that recorded after stirring the sample for 30 seconds at 1000 rpm using a rotor. Final foam volume is obtained as the average of ten repeats of measuring the foam volume upon stirring the sample for the 30 seconds at 1000 rpm.

We have also found that there is a correlation between squeakiness and contact angles of the silicas. Squeakiness has been found for those silicas having contact angles that range from 90 to 150, preferably from 100 to 140, and optimally from 105 to 125.

Advantageously, the compositions can further be formulated with a calcium salt to function as an adjunct squeakiness enhancing agent. Suitable, but not limiting, calcium salts may be selected from the group consisting of calcium chloride, calcium carbonate, calcium bicarbonate, calcium sulphate, calcium phosphate, calcium hydroxide, calcium citrate, calcium tartrate and combinations thereof. Amounts of the calcium salt may range from 0.001 to 0.6%, preferably from 0.01 to 0.3%, and optimally from 0.05 to 0.1% by weight of the composition.

The $C_8$-$C_{22}$ fatty acids may also be included in compositions of this invention. Suitable fatty acids are lauric acid, myristic acid, palmitic, stearic, oleic, linoleic, behenic and acid combinations thereof. Particularly useful are the $C_{12}$-$C_{14}$ fatty acids such as lauric acid and myristic acid. Amounts of the fatty acid may range from 0.1 to 15%, preferably from 0.5 to 10%, and optimally from 1 to 5% by weight of the composition.

Water may be present in the compositions in amounts from 5 to 95%, preferably from 50 to 90%, and optimally from 65 to 85% by weight.

Water soluble/dispersible polymers are an optional ingredient that may be included in the compositions of the invention. These polymers can be cationic, anionic, amphoteric or nonionic types with molecular weights higher than 1,000 Dalton. They are known to increase the viscosity and stability of liquid cleanser compositions, to enhance in-use and after-use skin sensory feels, and to enhance lather creaminess and lather stability. Amount of the polymers when present may range from 0.1 to 10% by weight of the composition.

Examples of water soluble/or dispersible polymers include the carbohydrate gums such as cellulose gum, microcrystalline cellulose, cellulose gel, hydroxyethyl cellulose, hydroxypropyl cellulose, sodium carboxymethylcellulose, methyl cellulose, ethyl cellulose, guar gum, gum karaya, gum tragacanth, gum arabic, gum acacia, gum agar, xanthan gum and mixtures thereof; modified and nonmodified starch granules and pregelatinized cold water soluble starch; emulsion polymers such as Aculyn® 28, Aculyn® 22 or Carbopol @Aqua SF1; cationic polymer such as modified polysaccharides including cationic guar available from Rhodia under the trade name Jaguar C13S, Jaguar C14S, Jaguar C17, or Jaguar C16; cationic modified cellulose such as UCARE Polymer JR 30 or JR 40 from Amerchol; N-Hance® 3000, N-Hance® 3196, N-Hance® GPX 215 or N-Hance® GPX 196 from Hercules; synthetic cationic polymer such as Merquat® 100, Merquat® 280, Merquat® 281 and Merquat® 550 sold by Nalco; cationic starches such as StaLok® 100, 200, 300 and 400 sold by Staley Inc.; cationic galactomannans such as Galactasol® 800 series by Henkel, Inc.; Quadrosoft® LM-200; and Polyquaternium-24. Also suitable are high molecular weight polyethylene glycols such as Polyox® WSR-205 (PEG 14M), Polyox® WSR-N-60K (PEG 45), and Polyox® WSR-301 (PEG 90M).

Water-soluble skin benefit agents may optionally be formulated into the compositions of the invention. A variety of water-soluble skin benefit agents can be used and the level can be from 0.1 to 50% but preferably from 1 to 30% by weight of the composition. These materials include, but are not limited to, polyhydroxy alcohols. Preferred water soluble skin benefit agents are glycerin, sorbitol and polyethylene glycol.

Water-insoluble skin benefit agents may also be formulated into the compositions as conditioners and moisturizers. Examples include silicone oils; hydrocarbons such as liquid paraffins, petrolatum, microcrystalline wax, and mineral oil; and vegetable triglycerides such as sunflowerseed and cottonseed oils.

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients. Preservatives are preferably employed in amounts ranging from 0.01% to 2% by weight of the composition.

A variety of other optional materials may be formulated into the compositions. These may include: antimicrobials such as 2-hydroxy-4,2'4'-trichlorodiphenylether (triclosan), 2,6-dimethyl-4-hydroxychlorobenzene, and 3,4,4'-trichlorocarbanilide; scrub and exfoliating particles such as polyethylene and silica or alumina; cooling agents such as menthol; skin calming agents such as aloe vera; and colorants.

In addition, the compositions of the invention may further include 0.5 to 10% by weight of sequestering agents, such as tetra sodium ethylenediaminetetraacetate (EDTA), EHDP or mixtures; opacifiers and pearlizers such as ethylene glycol distearate, titanium dioxide or Lytron 621 (Styrene/Acrylate copolymer); all of which are useful in enhancing the appearance or properties of the product.

All documents referred to herein, including all patents, patent applications, and printed publications, are hereby incorporated by reference in their entirety in this disclosure.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

It should be noted that in specifying any range of concentration or amount, any particular upper concentration can be associated with any particular lower concentration or amount.

The following examples will more fully illustrate the embodiments of this invention. All parts, percentages and proportions referred to herein and in the appended claims are by weight unless otherwise illustrated.

EXAMPLES

Evaluations of squeakiness were performed by use of a Tribometer UMT device. The procedure is described below.

Tribometer UMT Procedure

The Tribometer UMT is a device measuring loading force and friction force between upper and lower test specimens with a set of two dimensional force sensors. The equipment is available from the Center for Tribology, Inc., Campbell, Calif. 95008. A slider is utilized to move the upper specimen against the stationary lower specimen. The upper specimen is connected to a vertical linear motion system that has a travel length of 150 mm. Ultra-accurate strain gauge sensors perform simultaneous measurements of load and torque in two axes. Resolution is 0.00003% of the full scale and achieves very high repeatability. A normal load sensor provides feedback to the vertical motion controller, actively adjusting sample position to ensure a constant load during testing.

For the present experiments, a FL 50 g sensor was employed with either a 10 g or 20 g load. The sensor probe was fitted with a glass lens which was covered by a solid grip liner. Speed was set at 10 mm/s with a travel distance of 50 mm.

A synthetic substrate known as VitroSkin™ strip 3 cm×11 cm was wetted in water (about 45° C.) for 2 minutes and clamped onto a rubber plate. A sample (2 mg/cm$^2$) was placed on the surface of the VitroSkin™ and rubbed under water 10 times to achieve even distribution. Water was then added to the evaluation container and the probe head soaked under water. The probe was programmed to contact the VitroSkin™ with either a 10 g, 15 g or 20 g load and for rubbing onto the surface in one direction with 10 mm/s speed, raised up 10 mm and moved back to an initial position.

The probe was then rubbed on the VitroSkin™ for 40 times under water. Rubbing was stopped when friction exceeded the limitation weight (45 g), or after the stick-slip moved to a large intensity. The base line was a single application step before water wash.

The friction and loading force were then recorded. The mean friction force and the stick-slip amplitude could then be calculated.

Samples

A set of formulas were evaluated with the Tribometer UMT equipment. These formulas were combinations of certain additives combined into a control base that featured a syndet surfactant combination of sodium lauryl ether sulphate/cocoamidopropyl betaine (Control Base A) or sodium cocoyl glycinate/cocoamidopropyl betaine (Control Base B). The Control Base components are outlined in Table 1.

TABLE I

Control Base Compositions

| Component | Control Base A (Weight %) | Control Base B (Weight %) |
|---|---|---|
| Cocoamidopropyl Betaine | 4.8 | 4.8 |
| Sodium Laureth Sulfate | 4.0 | — |
| Sodium Cocoyl Glycinate | — | 4.0 |
| Lauric Acid | 1.0 | 2.4 |
| Glycerin* | 2.0 | 2.0 |
| Fragrance | 1.0 | 1.0 |
| Polyacrylic Thickener | 1.5 | 1.5 |
| Water | qs | qs |

*Additives replace glycerin on an equivalent weight basis.

Results of friction testing of various additives in Control Base A and B are reported in Tables II and III, respectively. Lower values for the "number of rubs for stick-slip" reflect improved squeakiness. Greater loads in the tribometer enhance the stick-slip properties.

TABLE II

Summary of Friction Results in Control Base A

| Additive | Tradename | Type | Additive Concentration (%) | No. Rubs For Stick-Slip | Tribometer Load g |
|---|---|---|---|---|---|
| None | | | | >20 | 20 |
| None | | | | >20 | 10 |
| Fumed Silica | Aerosil 200 ® | Hydrophilic (no coating) | 1.0 | 14 | 20 |
| Fumed Silica | Aerosil 200 ® | Hydrophilic (no coating) | 2.0 | >20 | 10 |
| Fumed Silica | Aerosil R972 ® | Hydrophobic | 1.0 | 4 | 20 |
| Fumed Silica | Aerosil R972 ® | Hydrophobic | 2.0 | 7 | 10 |
| Silica/Alumina | Aerodisp (WK341) | Cationic | 1.0 | 3 | 20 |
| Silicon Dioxide | Aerogel VM-2270 ® | Hydrophobic | 1.0 | 3 | 20 |
| Titanium Dioxide | MPY-100M | Hydrophobic | 2.0 | >20 | 10 |
| Boron Nitride | Boroneige 602-DMC3 | Hydrophobic | 2.0 | >20 | 10 |
| PTFE* | | Hydrophobic | 2.0 | >20 | 10 |
| Silicon Dioxide | | Hydrophilic | 2.0 | 16 | 10 |

*Polytetrafluoroethylene

TABLE III

Summary of Friction Results in Control Base B

| Additive | Tradename | Type | Additive Concentration (%) | No. Rubs For Stick-Slip | Tribometer Load g |
|---|---|---|---|---|---|
| None | | | | 18 | 20 |
| None | | | | 14 | 10 |
| Fumed Silica | Aerosil 200 ® | Hydrophilic (no coating) | 1.0 | 9 | 20 |
| Fumed Silica | Aerosil 200 ® | Hydrophilic (no coating) | 2.0 | >20 | 10 |
| Fumed Silica | Aerosil R972 ® | Hydrophobic | 1.0 | 5 | 20 |
| Fumed Silica | Aerosil R972 ® | Hydrophobic | 2.0 | 6 | 10 |
| Silica/Alumina | Aerodisp (WK341) | Cationic | 1.0 | 4 | 20 |
| Silica/Alumina | Aerodisp (WK341) | Cationic | 2.0 | 7 | 15 |
| Silicon Dioxide | Aerogel VM-2270 ® | Hydrophobic | 1.0 | 3 | 20 |
| Silicon Dioxide | Aerogel VM-2270 ® | Hydrophobic | 2.0 | 4 | 20 |
| Silicon Dioxide | Aerogel VM-2270 ® | Hydrophobic | 2.0 | 5 | 15 |
| Titanium Dioxide | MPY-100M | Hydrophobic | 2.0 | 20 | 10 |
| Boron Nitride | Boroneige 602-DMC3 | Hydrophobic | 2.0 | >20 | 10 |
| PTFE | | Hydrophobic | 2.0 | >20 | 10 |
| Silicon Dioxide | | Hydrophilic | 2.0 | 15 | 10 |

Control Base A as seen from Table II has poor stick-slip as indicated by the number of rubs being much greater than 20 in the Tribometer UMT Test. Hydrophilic fumed silicas do not significantly achieve any improved stick-slip. However, where the fumed silica has a coating to render the particles hydrophobic, such as with Aerosil R972® there is a marked change and stick-slip is observed. The number of rubs reduces from 14 down to 4 as the hydrophilic fumed silica is replaced by similar size hydrophobic silica. Similarly useful are cationic and hydrophobic silicas under the tradenames Aerodisp WK341® and Aerogel VM-2270®. No stick-slip improvement was observed with particles such as titanium dioxide. boron nitride or PTFE.

Control Base B itself exhibits a modest stick-slip performance. A hydrophilic fumed silica such as Aerosol 200® does not improve upon and at 2% is inferior to even the Control Base itself. Additives which do improve the stick-slip are hydrophobic fumed silica such as Aerosil R972®, Aerodisp WK341® and Aerogel VM-2270®. Again, titanium dioxide, boron nitride and PTFE were all non-effective to improve friction properties.

Contact angles for the silicas and other friction modifying additives are tabulated in Table IV.

TABLE IV

Contact Angle Correlations

| Additive | Tradename | Type | Size (microns) | Contact Angle (Degree) |
|---|---|---|---|---|
| Fumed Silica | Aerosil 200 | Hydrophilic | 0.012 | 14 |
| Fumed Silica | Aerosil 300 | Hydrophilic | 0.007 | 14 |
| Fumed Silica | Aerosil R972 | Hydrophobic | 0.016 | 110-120 |
| Fumed Silica | Aerosil R816 | Hydrophobic | 0.012-0.016 | 100-120 |
| Silica/Aluminum | Aerodisp (WK341) | Cationic | 0.14 | — |
| Silicon Dioxide | Aerogel (VM-2270) | Hydrophobic | 5-15 | 120 |
| Silicon Dioxide | | Hydrophilic | 1-5 | <20 |

Table IV reveals that hydrophilic fumed silica and non-fumed silicon dioxide (silica) with contact angles below 20 correlate to poor stick-slip properties as shown in the formulation results listed in Table II and III. By contrast, hydrophobic fumed silicas reveal contact angles above 100. These materials provided the stick-slip necessary for formulation squeakiness. Note the stick-slip results for these materials in Table II and III.

Clinical Study

A clinical study was conducted with 15 panelists. The panelists were requested to evaluate dragginess of various samples during rinsing in a cleansing experiment. The study was an alternative forced choice procedure. Sample products were presented in uniform 2 oz. bottles using sequential monadic randomized block design.

According to the protocol, a first sample product was placed on the left forearm and a second sample product in comparison on the right forearm. In alternating fashion, the panel rinsed the respective forearms in running water [34-36° C.] while holding their arm at a 90 degree angle. The sequence was repeated 5 times. The panelist was requested to evaluate during the procedure which arm had experienced the most dragginess during the rinse. The comparative first sample was Control Base B detailed in Table I. Sample 2 with 2% Aerogel VM-2270® displaced a small positive amount of dragginess, Sample 4 formulated with both hydrophobic silica and calcium salt displayed by far the most dragginess. The results of the Study are reported in the Table V.

TABLE V

Alternative Forced Choice Study/Clinical Study

| Sample No. | Sample Product | Wet Dragginess (d') |
|---|---|---|
| 1 | Control Base B | 0.0 |
| 2 | Control Base B with 2% Aerogel VM-2270 ® | 0.0609 |
| 3 | Control Base B with 0.1% calcium salt | −0.118 |
| 4 | Control Base B with 0.1% calcium salt and 2% Aerogel VM-2270 ® | 1.19 |

While the invention has been described in detail with reference to specific embodiments thereof, it will be apparent to one skilled in the art that various changes and modifications can be made therein without departing from the spirit and scope thereof.

What is claimed is:

1. A cleanser composition comprising:
   (i) from 0.01 to 5% by weight of a silica having a number average particle size ranging from 1 to 30,000 nm;

(ii) from 0.1 to 30% by weight of a non-soap synthetic surfactant; and wherein the composition exhibits a UMT Test number of rubs to stick-slip ranging from 1 to 12 under a 20 g load, and a foam volume ranging from 200 to 800 ml using a SITA Foam Tester, wherein the silica is a cationic silica.

2. The composition according to claim 1 wherein the synthetic surfactant is selected from the group consisting of cocoamidopropyl betaine, $C_8$-$C_{22}$ acyl glycinate salts, laurylether sulfate salts and combinations thereof.

3. The composition according to claim 2 wherein the synthetic surfactant is cocoamidopropyl betaine.

4. The composition according to claim 2 wherein the glycinate salt is sodium cocoyl glycinate.

5. The composition according to claim 1 wherein the UMT Test exhibits a number of rubs to stick-slip ranging from 3 to 10.

6. The composition according to claim 1 wherein the cationic silica has a contact angle that ranges from 90 to 120.

7. The composition according to claim 1 further comprising from 0.001 to 0.6% by weight of a calcium salt.

8. The composition according to claim 7 when the calcium salt is selective from the group consisting of calcium chloride, calcium carbonate, calcium bicarbonate, calcium sulphate, calcium phosphate, calcium hydroxide calcium citrate, calcium tartrate and combinations whereof.

9. The composition according to claim 7 wherein the calcium salt is present in the amount from about 0.01 to 0.3% by weight.

* * * * *

UNITED STATES PATENT AND TRADEMARK OFFICE
CERTIFICATE OF CORRECTION

| | | |
|---|---|---|
| PATENT NO. | : 8,648,024 B2 | Page 1 of 1 |
| APPLICATION NO. | : 13/370707 | |
| DATED | : February 11, 2014 | |
| INVENTOR(S) | : Chandra Sekhar Palla-Venkata et al. | |

It is certified that error appears in the above-identified patent and that said Letters Patent is hereby corrected as shown below:

On the Title Page, item [75], the first inventor's name should read --Chandra Sekhar Palla-Venkata--.

Signed and Sealed this
Third Day of June, 2014

Michelle K. Lee
*Deputy Director of the United States Patent and Trademark Office*